United States Patent [19]
Annino et al.

[11] Patent Number: 5,340,543
[45] Date of Patent: Aug. 23, 1994

[54] MODULAR GAS CHROMATOGRAPHY DEVICE

[75] Inventors: Raymond Annino, North Smithfield, R.I.; Edward L. Lewis, Sharon, Mass.; Dale E. Lueck, Chelmsford, Mass.; Matthew L. Phillips, North Easton, Mass.; Richard Villalobos, Duxbury, Mass.

[73] Assignee: The Foxboro Company, Foxboro, Mass.

[21] Appl. No.: 570,947

[22] Filed: Aug. 22, 1990

[51] Int. Cl.$^5$ ........................ G01N 30/02; G01N 31/00
[52] U.S. Cl. .......................................... 422/89; 422/83; 73/23.24; 73/23.35; 73/23.41; 73/863.83; 73/864.86
[58] Field of Search ............... 422/83, 89, 70; 55/386; 73/23.35, 23.42, 23.24, 23.41, 863.86, 863.72, 863.73, 864.83, 864.84; 138/43, 46

[56] References Cited

U.S. PATENT DOCUMENTS

| | | | |
|---|---|---|---|
| 2,833,311 | 5/1958 | Baldelli | 138/43 |
| 3,070,989 | 1/1963 | Dueker et al. | 73/23.35 X |
| 3,201,922 | 8/1965 | Villalobos | 73/23.42 X |
| 3,368,385 | 2/1968 | Harvey, Jr. | 73/23.41 X |
| 3,753,653 | 8/1973 | Brevia et al. | 422/89 X |
| 3,785,616 | 1/1974 | Moore | 138/43 X |
| 3,916,465 | 11/1975 | Jones | 73/23.35 X |
| 4,044,593 | 8/1977 | Haruki et al. | 73/23.1 |
| 4,057,998 | 11/1977 | Moreaux | 73/23.1 |
| 4,474,889 | 10/1984 | Terry et al. | 422/89 X |
| 4,634,434 | 1/1987 | Marino, Jr. et al. | 138/46 X |
| 4,935,040 | 6/1990 | Goedert | 55/386 X |
| 5,053,200 | 10/1991 | Schaeffer et al. | 422/83 |
| 5,105,652 | 4/1992 | Manfredi et al. | 73/23.250 |

FOREIGN PATENT DOCUMENTS

| | | | |
|---|---|---|---|
| 0092779 | 2/1983 | European Pat. Off. . | |
| 0057159 | 4/1984 | Japan | 422/89 |
| 1052997 | 11/1983 | U.S.S.R. | 422/89 |

OTHER PUBLICATIONS

Wilhite, W. F., "Developments in Micro Gas Chromatography", J. Gas Chromatog., Feb. 1966, pp. 47-50.
Terry et al, "A Gas Chromatographic Air Analyzer Fabricated on a Silicon Wafer", IEEE Transactions on Electron Devices, vol.-Ed-26, No. 12, Dec. 1979, pp. 1880-1886.
James B. Angell, et al., "Silicon Michromechanical Devices," *Scientific American*, vol. 248, No. 4, Apr. 1983, pp. 36-47.
Soheil Saadat et al., "Optimization of a Fortable Micro-GC For Analysis of Natural Gas," *Advances in Instrumentation*, vol. 39, No. 1, Oct. 1984, pp. 269-277.
International Search Report dated Oct. 27, 1992 for corresponding EPO application 92 300611.8.

*Primary Examiner*—Robert J. Warden
*Assistant Examiner*—Christopher Y. Kim
*Attorney, Agent, or Firm*—Jules Jay Morris; James M. Smith

[57] ABSTRACT

A chromatography device for separating sample fluids from carrier fluids and analyzing the sample is configured so that it is a modular unit. This modularity enables repairs to be quickly effected on the unit and also greatly simplifies the task of accessing the components of the chromatography cartridge. The modular chromatography cartridge is comprised of separation columns for separating the sample fluid from the carrier fluid. The cartridge additionally includes detectors for detecting distinguishing characteristics of fluids exiting the column. Further, the cartridge preferably includes valve assemblies for directing the flow of the carrier fluid and sample fluid throughout the cartridge and restrictors for adjusting the flow rate of the fluids as they flow through the cartridge. All of the components of the cartridge are configured upon a manifold. The manifold has a means for attaching the cartridge to fluid sources and support structure. The manifold enables the system to exhibit its modularity.

33 Claims, 16 Drawing Sheets

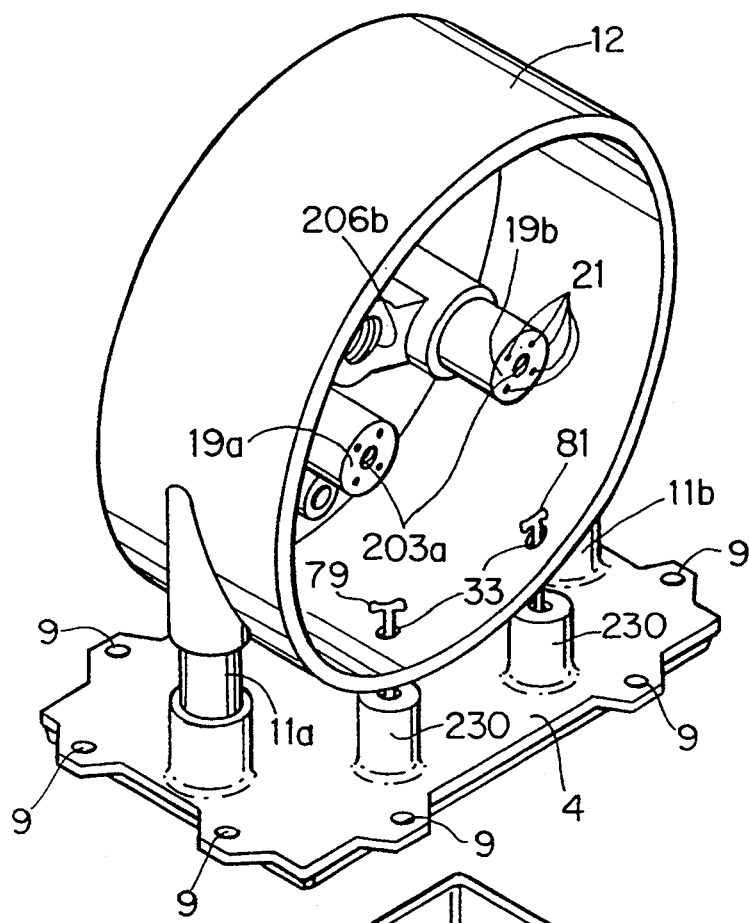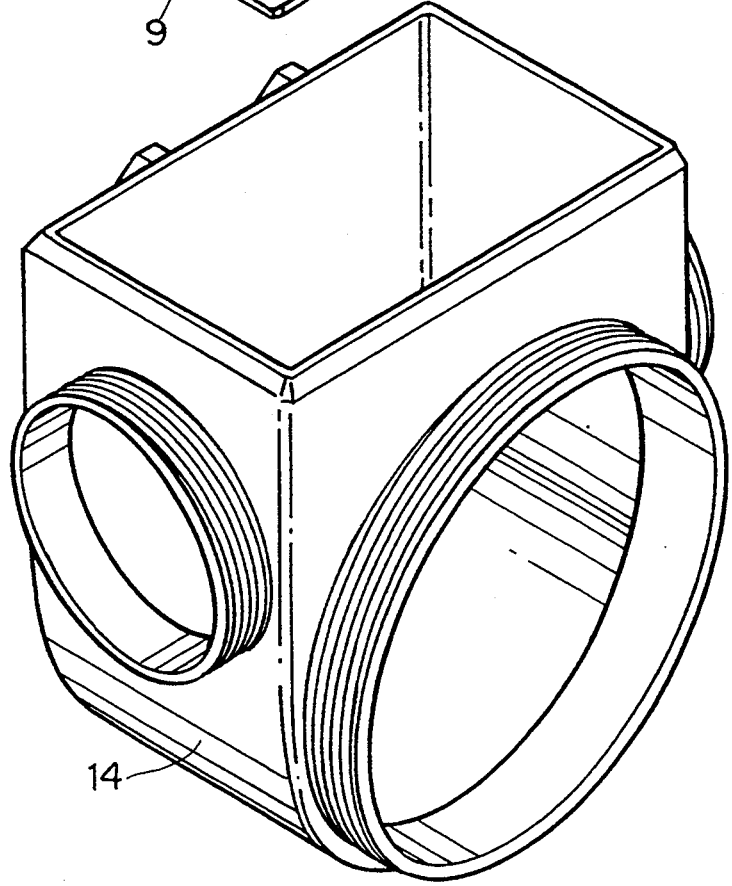
Fig. 3

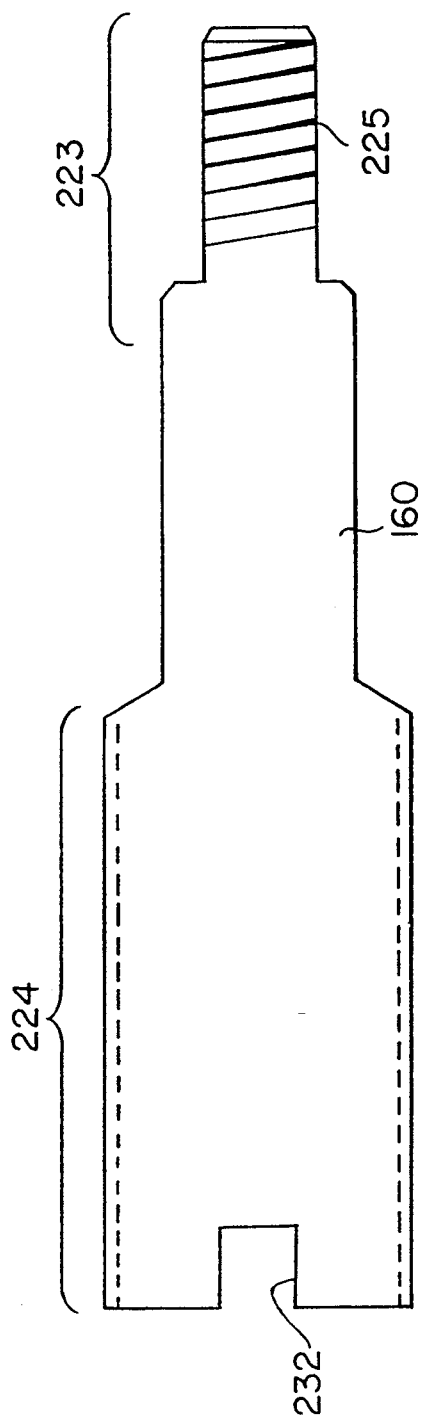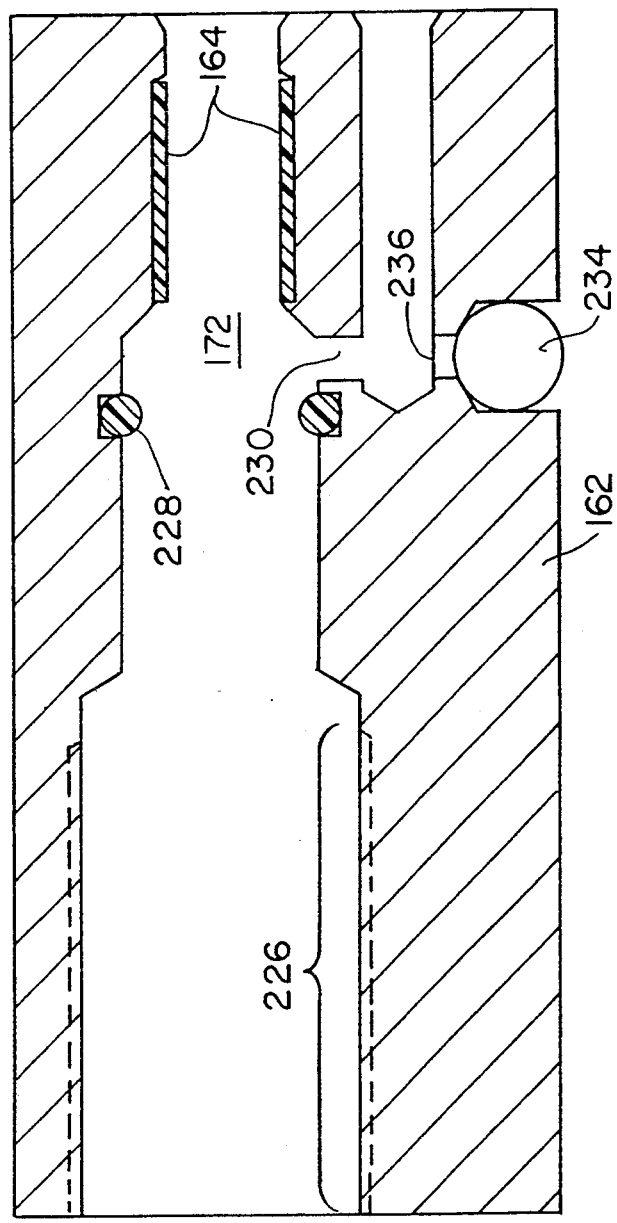

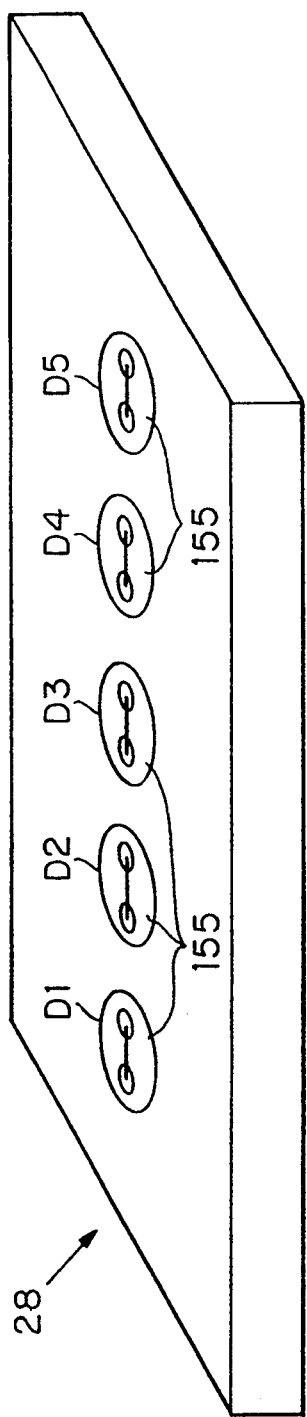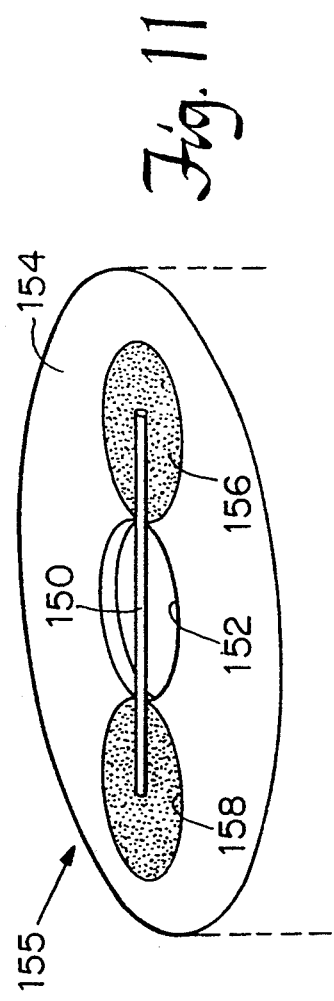
Fig. 10
Fig. 11

TYPICAL CHROMATOGRAM FROM MANIFOLD ASSEMBLY

MODULAR GAS CHROMATOGRAPHY DEVICE

BACKGROUND OF THE INVENTION

Gas chromatography is an analytical procedure used for the analysis of components of a complex sample mixture of gases. Gas chromatography physically separates the components of the complex sample mixture by exploiting the different affinities of the components to a stationary phase. Typically, the sample mixture is injected as a plug into a mobile fluid (carrier gas) and forced to flow through a tube (separation column) containing a stationary phase. The stationary phase may be either a liquid or a solid. Since each component of the sample has a different affinity to the stationary phase relative to its counterparts, each component is retarded to a different extent by the stationary phase in its passage through the tube. As a result, the components of the sample mixture emerge from the tube at different times.

Upon exiting the tube, the concentration of the components of the sample mixture are detected by detectors that are positioned to receive the gas leaving the tube. The detectors must be able to respond to property differences between a zone of carrier gas and a zone of carrier gas mixed with a sample component. A commonly used type of detector is the thermal conductivity detector (TCD). This type of detector measures thermal conductivity, which is an indication of a substance's ability to conduct heat. By determining the thermal conductivities of the component/carrier gas mixtures that exit the tube, the TCD is able to determine the concentration and composition of the components of the sample mixture.

The TCD is comprised of a wire filament to which a voltage is applied to generate a current in the filament. As current flows through the filament, the filament becomes heated. The rate at which such heat is dissipated from the wire is determined by the surrounding environment that encompasses the filament. Thus, a zone of carrier gas surrounding the filament dissipates heat from the filament at a different rate than a zone of carrier gas mixed with sample components. The different rates of dissipation of heat or thermal conductivity are used to distinguish sample components. Specifically, the filament is held at a constant temperature and resistance, and the power required to maintain the filament at the constant temperature is measured. The power measurements indicate the different thermal conductivities of the components and therefore, identify the components of a sample mixture.

The analysis of the sample mixture is developed over the period of time it takes for all of the sample components to emerge from the column, and thus, the analysis of a continuous process stream is somewhat outdated by the time the analysis is completed. Further, additional time is lost in analysis because, in most instances, the chromatograph is housed in an analyzer shack site at some distance from the sample point. The sample is piped from the sample point to the analyzer shack site. Thus, the time it takes to transport the sample from the sample point to the chromatograph also delays the analysis.

Current field gas chromatograph instrumentation packages are quite large and require an abundance of plumbing and electrical connections. The number of connections and the size of the chromatograph contribute to the difficulty of installing, repairing and removing them. Moreover, one must have expertise in the areas of electricity, plumbing and chromatography analysis to properly perform such removal. Matters are complicated by the environment in which the packages are mounted. Generally, the packages are mounted in hazardous areas where adherence to strict safety and electrical standards is vital. In view of these complications, the unit is generally not removed when repairs are necessary; rather, the sometimes delicate and complex repairs are performed in the field at the analyzer chromatograph shack site. The completion of such repairs usually requires the chromatograph to be put in an "off-line" condition for an extended period of time in which the plant from which the samples are taken may have to either shut down or run blind without vital instrumentation.

SUMMARY OF THE INVENTION

The present invention concerns a modular chromatography device for separating and analyzing the components of a complex sample mixture of gases. A chromatographic cartridge includes at least one column for separating the components of the sample fluids. It also includes a plurality of detectors for detecting distinguishing characteristics of the fluids that exit the separation columns. The columns and detectors are configured upon a manifold so as to form a modular unit that may be replaced easily. The manifold includes means for attaching the cartridge to fluid sources and to a support structure. Nevertheless, the connections are minimal and are easily disengaged. As such, the modular cartridge design greatly simplifies the tasks of performing repairs and replacing chromatography cartridges. Such ease in removal and repairs makes the cartridge especially useful in the field where a field technician is often confronted with difficult surroundings and hostile environmental conditions.

It is preferred that the column section of the cartridge contain at least one column having a stationary liquid phase coated on its walls. In particular, it is preferred that the stationary liquid phase is comprised of a methyl silicone stabilized by cross-linking. Other types of columns are envisioned by the present invention, and the choice of a column is dictated, in large part, by the gas separation application for which the column is being used. The diameter and length of the column and stationary phase film thickness that is used depends on the type of sample gas and type of carrier gas being used. In the preferred embodiment there are three columns for separating sample gases.

The preferred detectors of the present invention are thermal conductivity detectors. These detectors contain a filament that is heated by an electric current. The filaments have a diameter in the range of $10^{-6}$ meters and are preferably comprised of a material having a high thermal coefficient of resistance such as platinum or nickel. The detectors may also include wells under the filaments so that the fluids surround the filaments as they flow past the detectors. The detectors are preferably of miniature size so as to minimize the size of the detector cavity and to support high speed chromatographic analysis.

The gas chromatography cartridge also preferably includes a valve assembly for injecting the sample fluid into the carrier fluid within the cartridge. The valve assembly may be comprised of at least one slider for directing flow of fluids in the cartridge and at least one spring assembly coupled to the slide for biasing the slider. The valve assembly operates by sliding the slider valve face back and forth between alternative positions. The spring assembly is connected to the slider valve shaft which, in turn, is interfaced to a solenoid, located on the support structure, that moves the slider valve face into these alternative positions. Since the slider must slide to redirect carrier gas and sample gas flow, the slider is preferably comprised of a durable and slippery (i.e. low coefficient of friction) material. In the preferred embodiment there are two valve assemblies.

The gas chromatography cartridge also preferably includes restrictors. The restrictors are used to adjust flow rates for the various column configurations that are possible with this scheme of columns and valves. Such restrictors are preferably adjustable so that a wide dynamic range is provided. In the preferred embodiment the restrictors are comprised of a threaded portion having a variable depth groove for carrying fluid. This threaded portion is secured to a housing so that the length of the groove in the threaded portion, in which gas flows, is adjustable. It is preferred that the threaded region is secured to the housing by an additional threaded section. A port is provided to allow fluid to enter the first threaded position. Each restrictor preferably is miniature and includes a plastic sheath that surrounds the major body of the restrictor. The plastic sheath provides the gas tight seal between the gas and the walls. Its thickness is adjusted so as to compensate for expansion and contraction of the major body and the threaded restrictor with varying temperatures, and, thus, it aids in lessening the temperature sensitivities of the restrictor.

The sample and carrier fluid flow is directed in the chromatography device by the slider valves as previously mentioned. Initially, a slider valve is shifted to a first position so that any residual sample fluid in the chromatography device is flushed out of a detection path of the device by carrier fluid while the sample loop is being flushed with new sample. Subsequently, the slider valves are positioned so that the sample fluid is injected into the detection path and carried by the carrier fluid in a detection path for analysis. One valve arrangement causes the sample fluid to be passed through the first, second and third columns of the chromatography device. Other positions may also be provided to direct a portion of the sample components so that they bypass a separation column.

BRIEF DESCRIPTION OF THE DRAWINGS

FIG. 3 illustrates a partially exploded front view of the unit with the environmental shroud, front face and access plates removed.

FIG. 9a and 9b illustrate the components of the restrictors.

FIG. 10 depicts the detector block.

FIG. 11 shows a single detector.

DETAILED DESCRIPTION OF THE PREFERRED EMBODIMENT

In accordance with the present invention, a gas chromatography device is configured to include a modular chromatographic cartridge that may be quickly and easily replaced by another suitable modular replacement cartridge. The modular cartridge is lightweight and portable. It is made up of a number of components including a plurality of miniature detectors, miniature separation columns, miniature restrictors and miniature valves. The modularity is achieved by configuring the components of the cartridge on a single manifold and making all necessary connections to these components through the manifold. The miniaturization and modularity enables the cartridge to be installed adjacent to the sampling point and, thus, decreases the delay time for analysis. The modularity also allows a cartridge that is in need of repair to be quickly and easily replaced with a replacement cartridge. This allows analysis to continue while repairs are performed on the defective cartridge back at a remote repair site.

Gas Chromotagraph Field Unit

Figure 1:
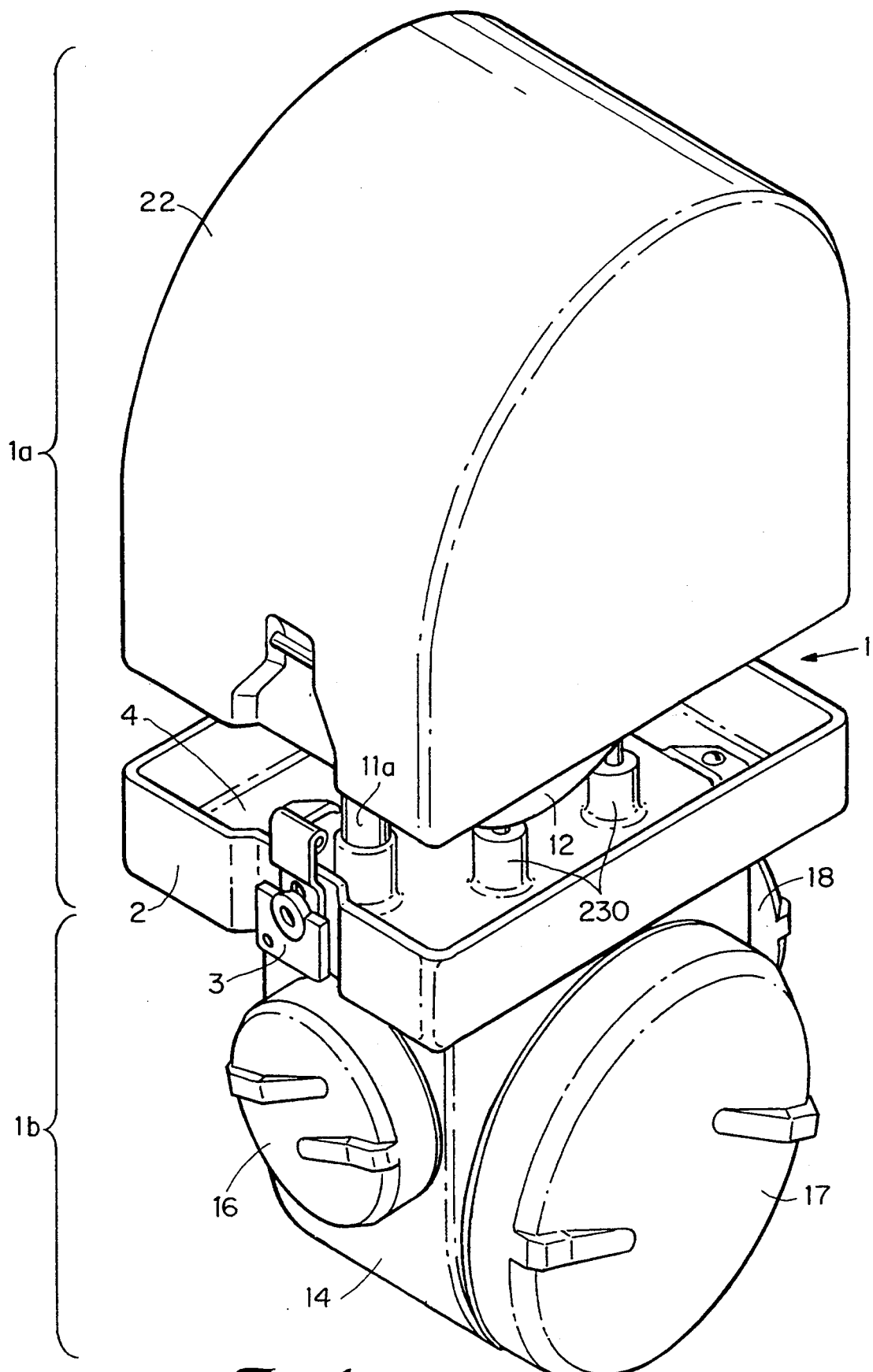
FIG. 1 is a perspective view of the field unit that houses the modular gas chromatography cartridge and associated electronics.
Figure 2:
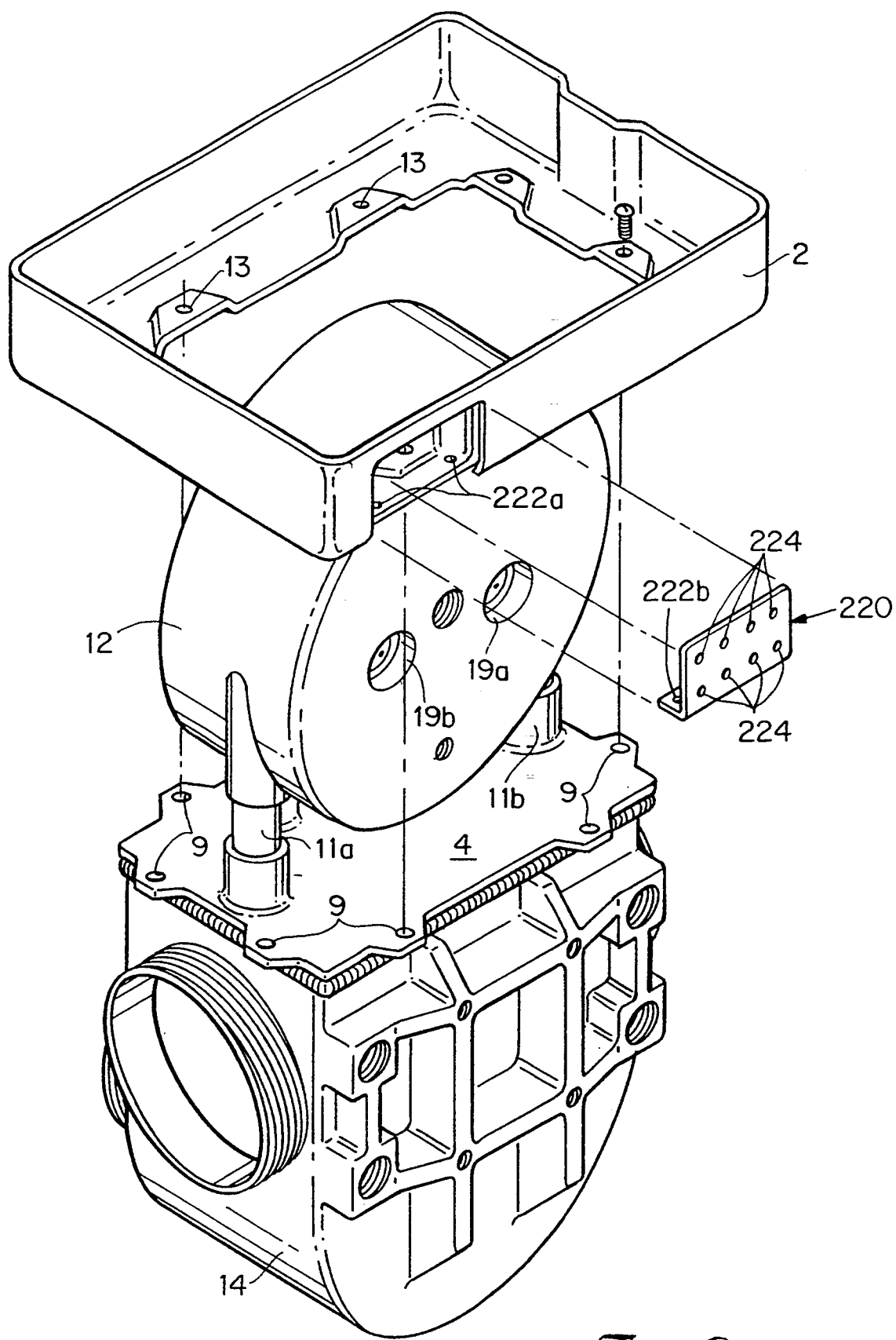
FIG. 2 is a partially exploded rear view of a portion of the unit of FIG. 1 with the environmental shroud removed.
Figure 4:
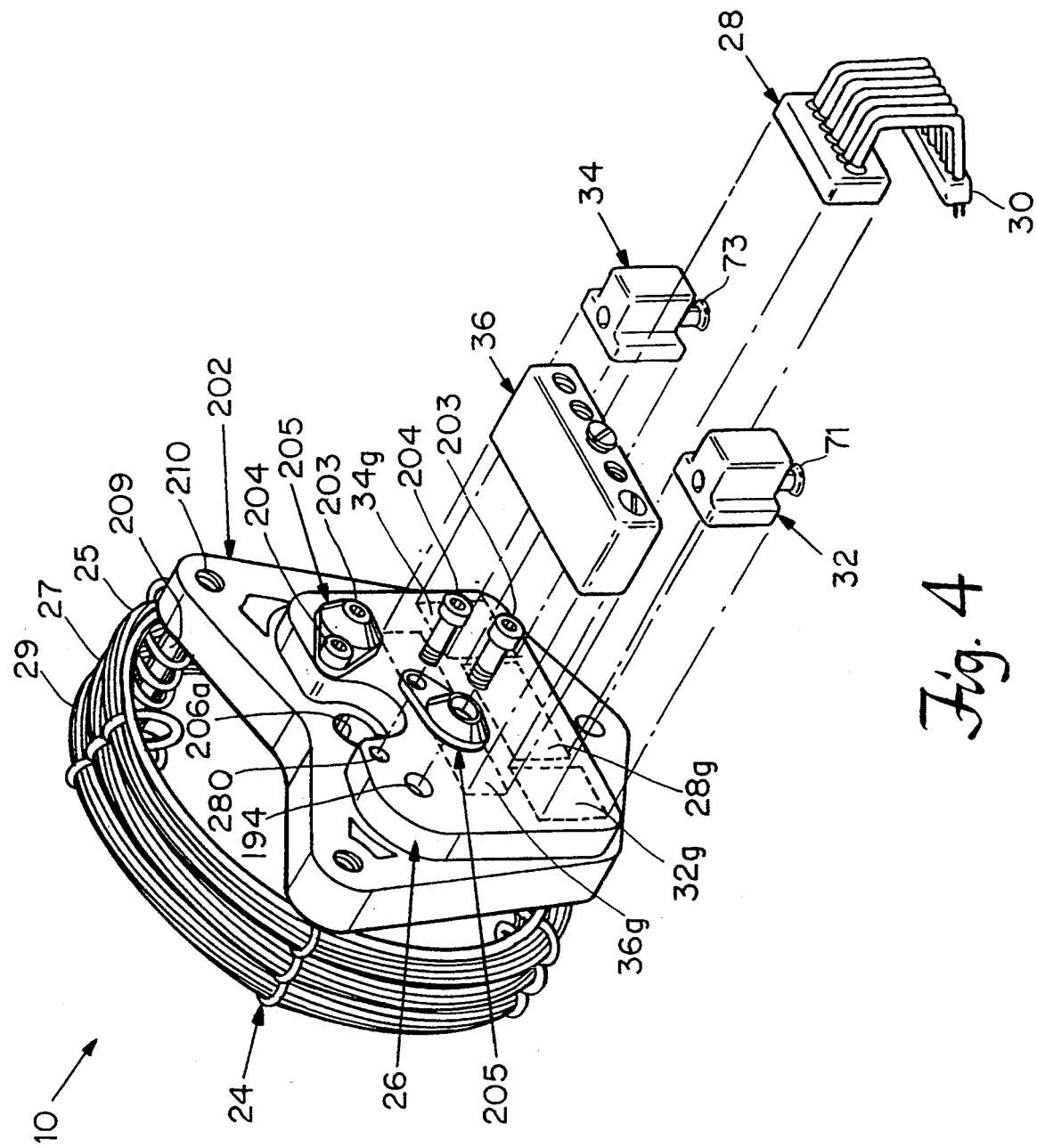
FIG. 4 shows a partially exploded view of the components of the gas chromatography cartridge that fit into the oven housing of FIG. 3.

The chromatography cartridge is positioned in a larger gas chromatograph field unit 1 (see FIGS. 1, 2 and 3). The field unit 1 provides a stable environment in which the cartridge can be operated and provides the necessary electric circuitry and gas connections to enable chromatographic analysis to be performed. The field unit 1 is divided into an upper portion 1a and a lower portion 1b that are separated by the base plate 4. The upper portion 1a consists of the area bounded by an environmental shroud 22 and a base plate 4. The upper portion 1a holds the gas chromatography cartridge 10 (FIG. 4). The lower portion constitutes the area lower housing 14 and the base plate 4. The lower portion 1b of the unit is used to house electronics that support operation of the chromatography cartridge 10.

As shown in FIG. 2, the upper portion 1a of the unit contains a circular oven housing 12 that surrounds and is coupled to the gas chromatography cartridge 10 (FIG. 4). The oven housing 12 includes a number of electrical heaters placed within its walls to regulate the temperature of the environment that surrounds the chromatography cartridge. It is important that the chromatography cartridge be disposed within a thermally controlled environment because temperature significantly affects the detection analysis. In particular, temperature affects the separation of the component gases by separation columns. Temperature also affects detectors used to detect the sample components and carrier gas, especially thermal conductivity detectors. Consistent temperature provides for both detection stability and retention time stability of samples as they pass through the columns. Without such retention time stability, comparisons and complete analysis of data becomes difficult because the effect of varying temperature must be taken into account.

The oven housing 12 is positioned above the base plate 4 by standoffs 11a and 11b. The standoffs 11a and 11b help to isolate the oven assembly 12 from other components of the system. The standoffs 11A and 11B are comprised of material that has low thermal conductivity to limit thermal communication between the upper portion 1a and the lower portion 1b of the unit. As such, the upper portion 1a may be heated to a temperature that is appropriate for analyzing gas samples without simultaneously heating the lower portion. This isolation prevents the oven 12 from deleteriously heating the electronic components held in the lower portion 1b and also provides an isolated environment in which the temperature of the cartridge can be closely regulated.

The environmental shroud 22 (FIG. 1) in the upper portion 1a of the unit is coupled to a base 2. The environmental shroud 22 shelters and isolates the oven assembly 12 (FIG. 2) from the outside environment and provides thermal insulation so that the oven assembly 12 can provide a closely regulated thermal environment for the gas chromatography cartridge. The shroud 22 is secured to the base 2 via a latch 3 (FIG. 1). The base 2, in turn, is secured to a base plate 4 (FIG. 2) by screws that pass through holes 9 in the base plate 4 and holes 13 in the base 2.

The oven housing 12 includes two bosses 19a and 19b (FIG. 3) for connecting lines of carrier gas and sample gas to the cartridge 10. These bosses 19a and 19b include interfaces that connect with ports in the cartridge manifold 26 to allow gases to flow in and out of the cartridge. An internal tube (not shown) is provided for each port to carry gas. Since there are four ports 21 at each boss 19a, 19b, there are a total of eight internal tubes, only seven of which are connected to the ports. These seven ports are also matched with a corresponding set of seven external gas carrying tubes (not shown) that connect to plate 220. Bulkhead connectors couple the internal tubes to the external tubes via holes 224 provided in the plate 220 (FIG. 2). The plate 220 is secured to the base 2 via screws that pass through matching holes 222a and 222b.

Holes 33 (FIG. 3) are also provided in the oven housing 12 and plate 4 for solenoid shafts 79 and 81 to pass. The role of the solenoids in the system will be described in more detail below.

The base 2 (FIG. 2) is, in turn, secured to a lower housing 14. The lower housing 14 forms an explosion proof cavity that enhances the safety of the assembly. It includes threaded access plates 16, 17, and 18 (FIG. 1). Located inside the lower housing 14 is a solenoid, solenoid drive and electrical circuitry to power the cartridge 10 (FIG. 4) and to process data derived from the cartridge.

The field unit 1 is designed so that the upper portion 1a is separate from the lower portion 1b. This separation of the two portions 1a and 1b provides safety benefits. One of the primary benefits of the separation is that the chromatography cartridge can be replaced without breaching the interface to the lower portion 1b of the unit. As such, during replacement of the cartridge, the high power electronic components in the lower portion 1b are not exposed to potentially explosive sample gas from the chromatography cartridge or the outside environment. The potential for an explosion stems from the presence of potentially explosive gases that are passed through the chromatography cartridge 10; hence, exposure of these gases to a spark or other ignition source could produce an explosion. To prevent possible explosions in the upper portion 1a, the upper portion 1a is created as an intrinsically safe environment (i.e. the explosive gases are not exposed to any possible ignition source). Specifically, the electrical components in the upper portion only operate at a very low power level which is insufficient to spark an explosion. This characteristic eliminates the need for powering down the system when a faulty chromatography cartridge is replaced.

Moreover, additional safety is achieved by making the lower housing 14 explosion proof. It is, therefore, certain that any such explosion would produce no damage outside the interior of the sealed environment. The combination of these attributes leads to a system that is safe yet easier to access than the gas chromatography systems that are currently available.

Chromatography Cartridge

FIG. 4 shows a partially exploded view of the gas chromatography cartridge 10. The cartridge 10 includes a chassis plate 202 which serves as a skeletal structure for the other components of the chromatography cartridge 10. The chassis plate 202 is coupled to a wire cage 24 that holds three separation columns 25, 27 and 29 as will be described below. It should be noted, nevertheless, that a different number of columns may be loaded into the cage 24. The number of columns used is dictated by the gas analysis application.

Coupled to the chassis plate 202 is the manifold 26. The manifold 26 is secured to the chassis plate 202 via bolts 203 and 204 which pass through holes 194 and 195, respectively in the manifold 26 to the chassis plate 202. Securing plates 205 are provided, as shown, to aid in securing the screws 203 and 204 and to prevent damaging of the manifold 26.

The chromatography cartridge 10 further comprises two slider valve assemblies 32 and 34 attached to the manifold 26 at pads 32g and 34g. These assemblies 32 and 34 dictate the direction of flow of the gases throughout the chromatography cartridge 10.

Another component configured on the manifold is a detector block 28. This block 28 houses the detectors that detect the primary components of the sample gas as they flow past the detector. A gasket 28g aids in creating a proper seal between the detector block 28 and the manifold 26. An electrical connector 30 is attached to the detector block 28. Electrical connector 30 enables external electrical communications between the detectors and electronics in the lower housing 14. This electrical connector 30 operates only at low power levels that are consistent with the requirements necessary to maintain an inherently safe environment. The electrical connector is coupled to another connector (not shown) in the oven housing 12. The additional connector has wiring that runs from the oven housing 12 down into the lower portion 1b of the unit via standoff 11a into which the wiring is sealed. This approach preserves the integrity between the portions 1a and 1b by allowing the chromatography cartridge to be decoupled (including the electrical connector 30) with out breaching the interface between the upper portion 1a and the lower portion.

A block of restrictors 36 is also provided to regulate the pressure of gas through the system. A gasket 36g seals the block of restrictors to the manifold. Often times, it is desirable to bypass a given separation column. Such bypassing, however, affects the flow rate of the gas as it flows in the chromatography cartridge 10. In order to maintain equal flow rates for accurate detection of carrier gas through the alternative pathways, the resistance of each pathway must be balanced. The restrictors 36 provide this balance and are adjusted to generate the pressure drop that would be experienced if the columns were not bypassed. The restrictors 36 are necessarily adjustable to cover a wide dynamic range. The wide dynamic range is desirable because different types of columns will produce different pressure drops. Thus, absent the wide dynamic range, different restrictors would be required for different column configurations.

The cartridge 10 is connected to the oven housing 12 via a bolt (not shown). This bolt passes through a hole 206a in the chassis plate 202 and a corresponding hole 206b in the oven housing 12 (FIG. 3). The remaining connections to the oven housing 12 are achieved by bolts 203 that pass through the manifold 26 and chassis plate 202 into threaded holes 203a provided in the two bosses 19a and 19b (FIG. 3). Thus, removal and connection of the cartridge is readily achieved due to the minimal number of connections.

A more detailed description of the major components of the chromatography cartridge follows.

Chassis Plate

Figure 5:
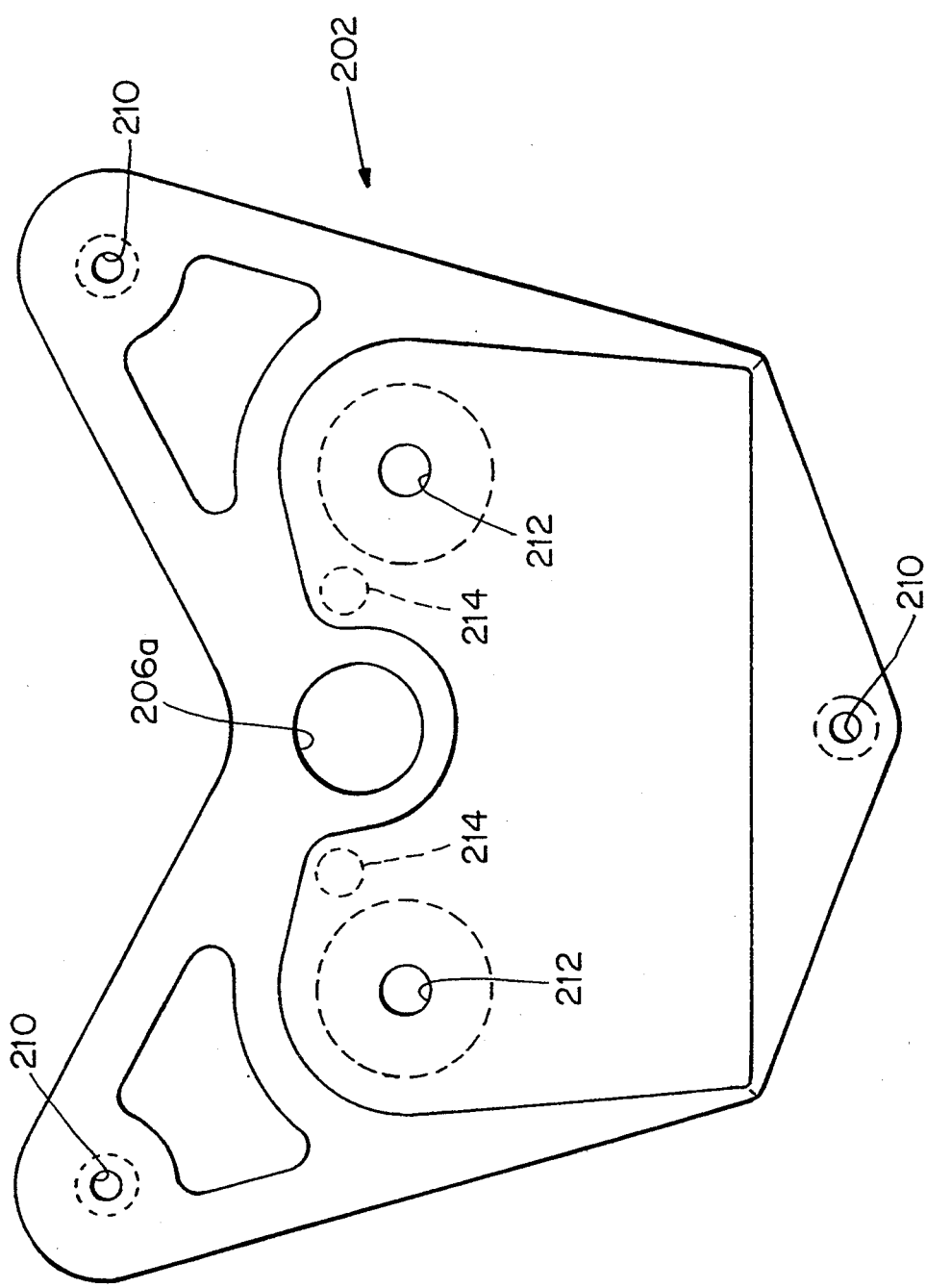
FIG. 5 depicts the chromatography cartridge chassis plate.

The chassis plate 202 to which the manifold 26 is coupled is shown in FIG. 5. FIG. 5 shows the front face of the chassis plate 202 relative to the ceramic manifold 26. The chassis plate 202 is secured to the wire cage 24 via securing rods 209 (FIG. 4) that pass through holes 210. The chassis plate also includes hole 206a (previously described) which accepts a bolt that secures the cartridge 10 to the oven housing 12. The holes 212 accept bolts 203 (FIG. 4) that are threaded into the bosses 19a and 19b (FIG. 3). Similarly, holes 214 are threaded to accept bolts 204 (FIG. 4).

Manifold

The manifold 26 is preferably made from ceramic material, although other materials that do not interfere with chromatographic performance are equally viable alternatives. As will be described in more detail below, the ceramic manifold 26 contains fluid conduits and acts as a substrate upon which other cartridge components are configured. The manifold 26 is made from a front ceramic plate 26a (FIG. 6a) and a rear ceramic plate 26b (FIG. 6b) that are initially in a green state. These two ceramic plates are subsequently fired and thus, bonded together to form a single manifold. There are channels provided in the ceramic plates 26a and 26b so that when they are bonded together, conduit paths are formed.

Figure 6A:
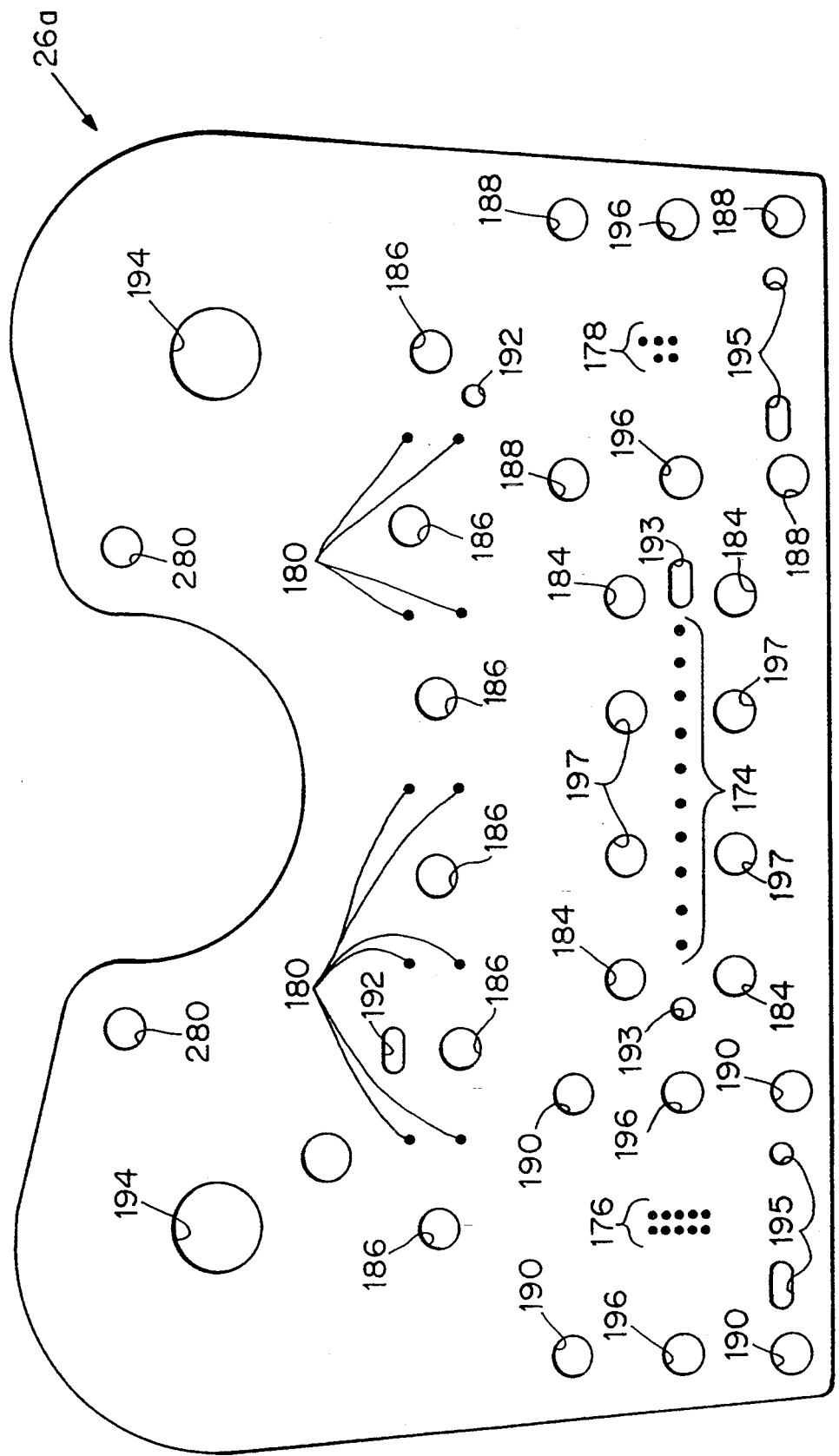
FIG. 6a, 6b and 6c depict the first and second plates of the ceramic manifold of the chromatography cartridge of FIG. 4.
Figure 6B:
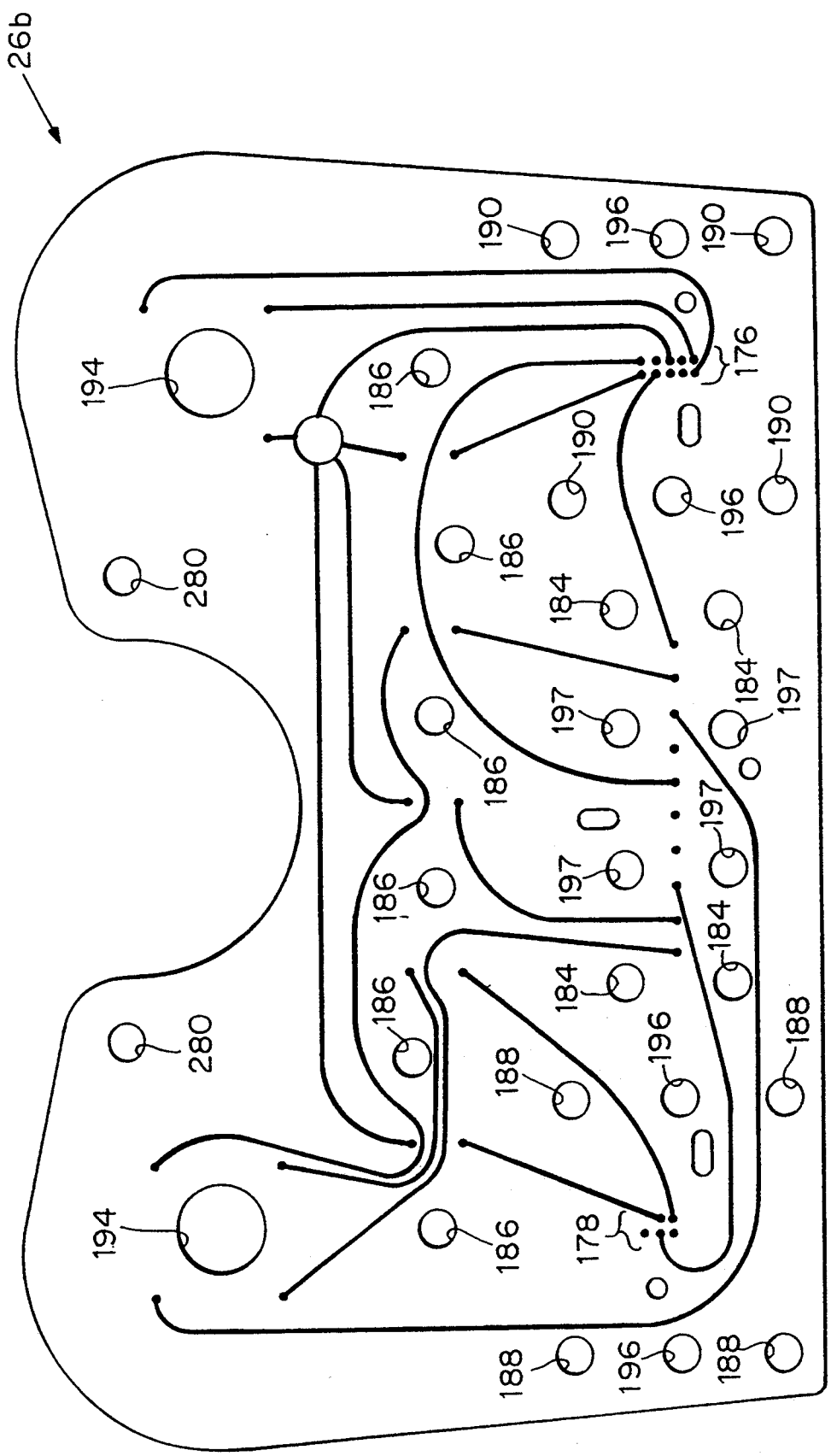

FIGS. 6a shows the top face of the front plate 26a and FIG. 6b shows the mating face of the rear plate 26b of the ceramic manifold 26. Each of the plates 26a and 26b has a length of approximately 3.5 inches and a height of approximately 2.5 inches and a thickness of approximately 0.08 inches. Each contains a number of holes that act as gas ports for the components that are coupled to the manifold. Specifically, holes 174 are gas ports that enable the detectors 28 to be interfaced with the manifold. Holes 176 and 178 are gas ports for the valves 32a and 34a, respectively. The holes 180 are used as gas ports by the restrictors 36. In addition holes 194 are provided to mount the manifold 26 and chassis plate 202 to the oven housing 12.

Other holes are provided for different purposes. In particular, some holes are provided for securing the components to the manifold 26. For instance, holes 192 mate with circular pins to properly position the restrictor block 36 to the manifold 26. Additional holes 186 are used to secure the restrictor assembly to the manifold 26. Similarly, holes 184 are used to secure the detector block 28. Dowel holes 193 are provided to position the detector block 28. Holes 188 and 190 are used to hold the two valve assemblies 32 and 34 to the manifold 26a and 26b. Holes 280 are used to receive dowels to assure alignment of the valves over the proper ports in the manifold furthermore, holes 196 and 197 receive the column mounting block bolts that secure the column mounting blocks to the other side of the manifold 26b.

FIG. 6b shows the mating face of the back plate. FIG. 6b not only depicts the holes in the manifold 26 but also shows the gas paths through which the gas may travel from the various gas ports depicted in FIGS. 6a and 6b. These paths are configured only on the mating face of the back plate 26b of the manifold.

Figure 6C:
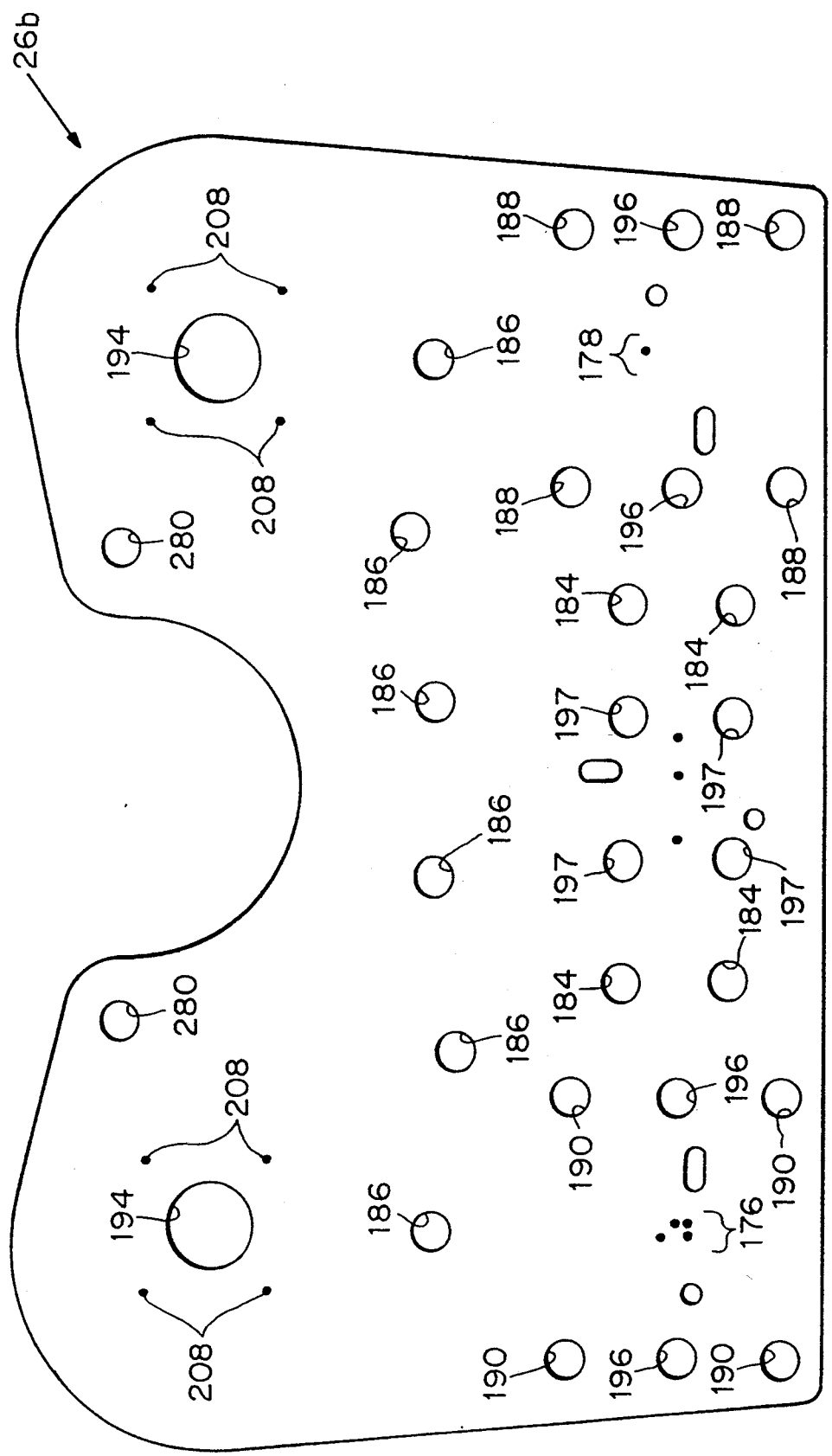

FIG. 6c shows the back face of the back plate 26b. The correspondence with the front face of the back plate (FIG. 6b) is evident. Of particular interest, however, are the gas ports 208. These ports 208 abut the bosses 19a and 19b of the oven housing 12. A gasket is provided to assure that a proper seal is formed between the manifold 26 and bosses 19a and 19b. The carrier gas and sample gas enter the manifold 26 via these ports 208 and are distributed.

Slider Valves

Figure 7:
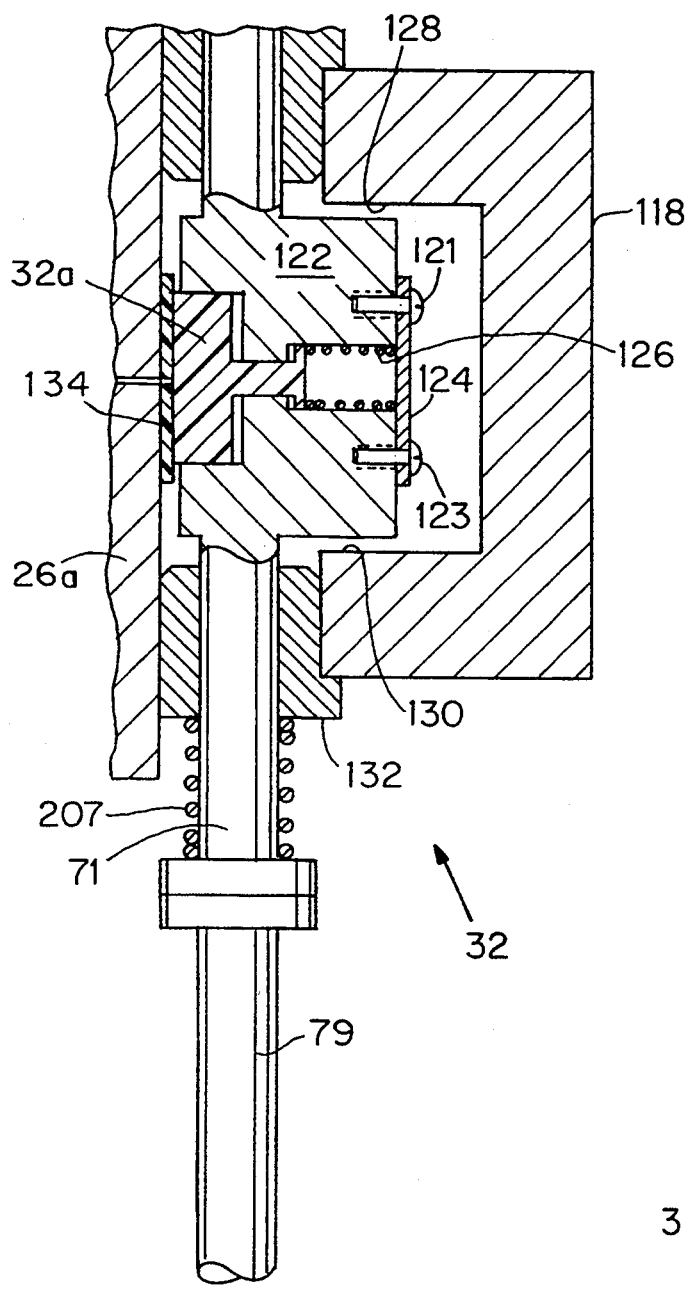
FIG. 7 illustrates a cross-sectional view of a slider valve assembly which is positioned adjacent to the chromatography cartridge.

FIG. 7 depicts a cross-sectional view of the valve assembly 32 from a partially exposed side view. Assembly 34 is identical to assembly 32, and both valve 32 and 34 are assemblies designed for long life (i.e. approximately 2,000,000 cycles). The valve assembly 32 includes a valve housing 118 and a slider housing 122. During operation of the slider 32a the slider housing 122 moves within the valve housing 118 and across the surface of the manifold 26a. The slider housing 122 may assume one of two positions. These positions (such as previously described) are one millimeter apart in the preferred embodiment. The movement of the slider housing 122 is limited by surface stops 128 and 130 of the valve housing 118.

Movement of the slider housing 122 is achieved with the assistance of solenoids that are located external to the chromatography cartridge 10 in the lower portion of the assembly 1b (FIG. 1). Shafts 79 and 81 of the solenoid extend to directly abut shafts 71 and 73 of the valve assemblies 32 and 34 (FIG. 4). The solenoid housings 230 are shown in FIGS. 1 and 3. The placement of the solenoid in the lower portion 1b eliminates the possibility of the high powered solenoid being exposed to potentially explosive gases present in the upper portion of the unit 1. Hence, the safety of the system is preserved. The solenoid shafts 79 and 81 pass through holes 33 to abut the valve shafts 71 and 73, respectively, (see FIG. 3). As depicted in FIG. 7, the solenoid shaft 79 pushes the spring loaded valve shaft 71 to move the valve into appropriate position. Shaft 71 is biased by a spring 207 that exerts outward pressure towards the solenoid shaft 79. Movement of the shaft 71 results in corresponding movement of the slider housing 122. The solenoid is a locking solenoid such that once the shaft 79 is driven into a given position, the shaft 79 is held in that position. A bushing 132 guides the shaft 71. This bushing 132 is preferably made of a long wearing material such as Vespel sold by Dupont.

The slider housing 122 includes spring 126 held in place by a spring cap 124. The cap 124 is attached to the slider housing 122 by two screws 121 and 123. The spring 126 is used for exerting a force on the slider 32a against the front plate 26a of the manifold to minimize gas leakage. The tension that the spring 126 exerts on the slider valve face 32a may be adjusted by changing springs. The slider 32a is preferably made of a long wearing slippery material such as "Rulon" produced by Dixon Industries Corporation.

The activity of the solenoid is dictated by control logic located in the lower portion of the system. The solenoid shaft 79 may be pushed or released in accordance with dictates of the control logic for moving the slider 32a to appropriate positions. This control logic preferably resides in the same data processing system that is used to analyze the data produced by the chromatography cartridge 10. Although the discussion has been limited to slider valve assembly 32 it should be born in mind that the control logic also controls assembly 34 which is comprised of identical components.

Figure 8:
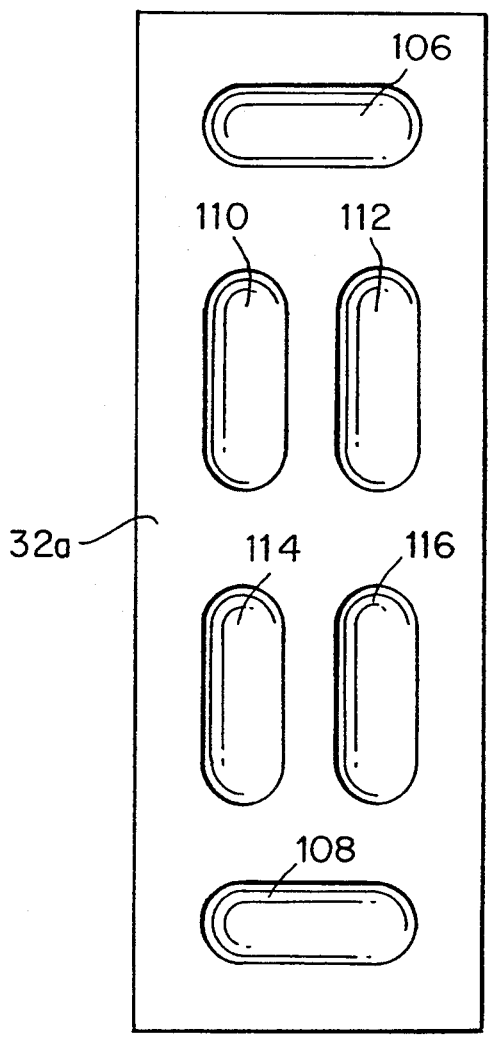
FIG. 8 shows a slider valve orifice plate.

The face of slider 32a, which is shown in FIG. 8, has two horizontally oriented pill shaped cavities 106 and 108 at its top and bottom, respectively. Located between the two horizontally oriented pill shaped cavities 106 and 108 are four vertically oriented pill shaped cavities 110, 112, 114 and 116. These cavities are aligned in pairs. The first pair is comprised of cavities 110 and 112, and the second pair is comprised of cavities 114 and 116. The vertical pairs are positioned parallel to each other. Moreover, cavity 110 is positioned directly above cavity 114 and cavity 112 is positioned directly above cavity 116 as shown in FIG. 8. Additionally, each of the vertical cavities is positioned so that its outermost edge is tangentially aligned with outermost edges of the horizontal cavities 106 and 108. During operation, the cavities of the sliders 32a and 34a are shifted back and forth to connect gas ports in the manifold 26 as will be described below.

Restrictors

Referring to FIGS. 9a and 9b, the restrictors R1–R5 (FIG. 12) used in the preferred embodiment are comprised primarily of two components: a housing 162 (FIG. 9b) and an insert 160 (FIG. 9a) which is designed to fit into the housing 162. The insert 160 includes a major body 223 having a spiral groove or scratch 225 in its surface through which gas flows. The depth of the scratch 225 of the major body 223 increases along its length. The insert 160 also includes a threaded portion 224 having threads that screws into a mating threaded portion 226 of the housing 162. An o-ring 228 is partially recessed in the insert 160 to create a gas seal with housing 162. The seal prevents gas that enters the housing 162 via gas port 230 from flowing in the direction of threads 226.

Figure 14:
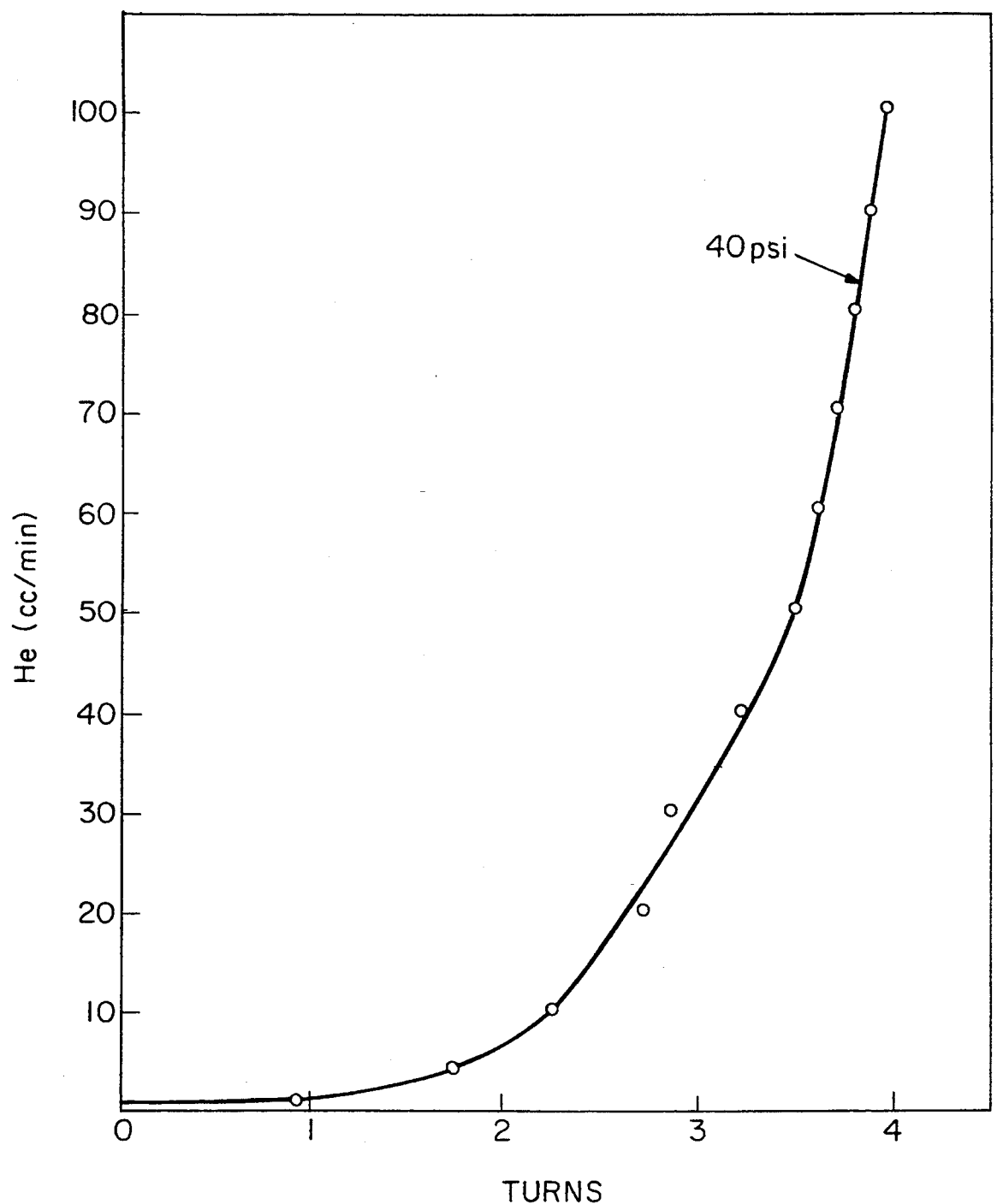
FIG. 14 shows a typical calibration curve for the restrictors.

Gas first enters the restrictor via the port 230 and enters an initial receiving area 172. The gas then flows down the groove of the major body 223. The length of the groove 225 within a plastic sheath 164 which restricts flow may be adjusted by screwing or unscrewing the insert 160 relative to the housing 162. A screwdriver slot 232 is provided in the insert 160 to facilitate such adjustment. Because the depth of the groove increases along its length, the pressure drop of the gas across the length of the groove varies nonlinearly with changes in length. In general, the groove is deeper near the distal end of the major body 223. By providing a variable coefficient of resistance per unit of length, a large dynamic range of flow adjustment is accomodated over a short distance. See FIG. 14 for a typical calibration curve of the restrictors.

The plastic sheath 164 compensates for restriction and contraction of both the housing 162 and the major body 223 due to changes in temperature. The sleeve 164 is configured so that the expansion and contraction of the major body 223 and housing 162 due to changes in temperature are equalized by the sleeve 164 to prevent gaps from forming between the major body 223 and sleeve 164.

In this embodiment, the opening 230 is formed by cross drilling, hence, the housing 162 also includes a ball seal 234 at opening 236.

Detectors

A more detailed view of the detector block 28 is shown in FIG. 10. The detector block 28 is comprised of five identical miniature detectors 155 numbered D1, D2, D3, D4 and D5. FIG. 11 shows a more detailed view of sample detector 155 corresponding to any of the detectors D1–D5. It has a one micron diameter platinum wire 150 located across a well 152 formed in a glass substrate 154. The well has a diameter of 0.034" and is 0.005" deep. The platinum wire 150 is secured in contact regions 156, 158.

During operation, a current is applied through the wire 150 in such a manner so as to keep the wire at a constant resistance. As gaseous fluids pass over and under the wire 150, heat generated by the wire is conducted to the passing gas at a rate which corresponds to the thermal characteristics of the gas. The rate of this thermal conduction would normally directly affect the resistance of the wire 150. However, an electronic servo loop adjusts the current to keep the resistance of the wire filament constant. The resulting measured change in supplied power produces the chromatographic signals used to identify and quantify components of the sample gas as previously described.

Columns

The columns 25, 27 and 29 (FIG. 4) in which the separating process occurs may be of many different types. In the preferred embodiment liquid stationary phase columns are used. Generally, the application dictates the type of column that is used. The columns are preferably 0.1 to 0.25 millimeters in inside diameter and include a stationary liquid phase having a low vapor pressure such as methyl silicon. The liquid phases are between 0.10 microns and 2 microns thick. The length of the column and the type of phase used are both dictated by the application.

Cartridge Operation

Figure 12A:
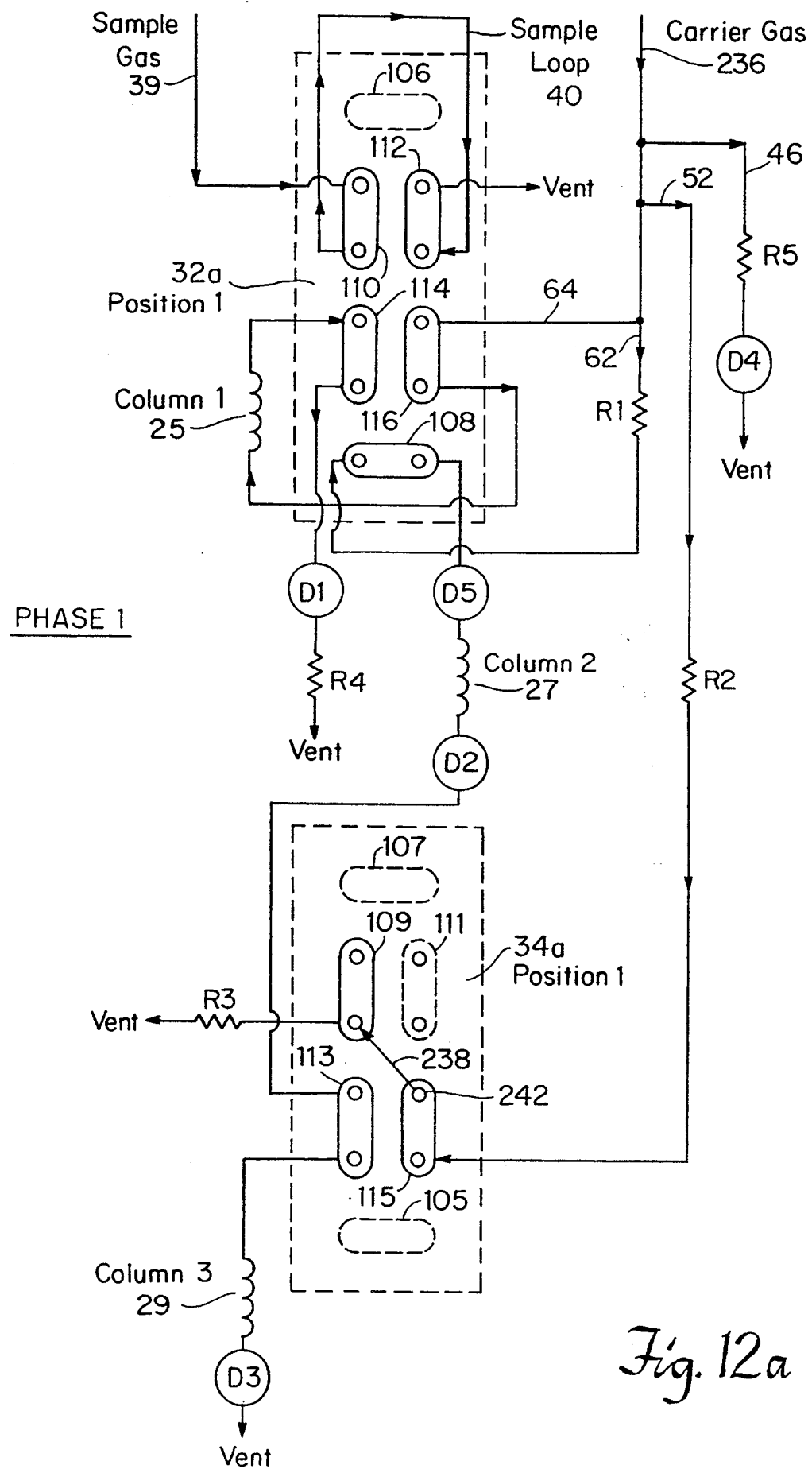
FIGS. 12a, 12b and 12c are schematics of the respective phases of operation of the cartridge.
Figure 12B:
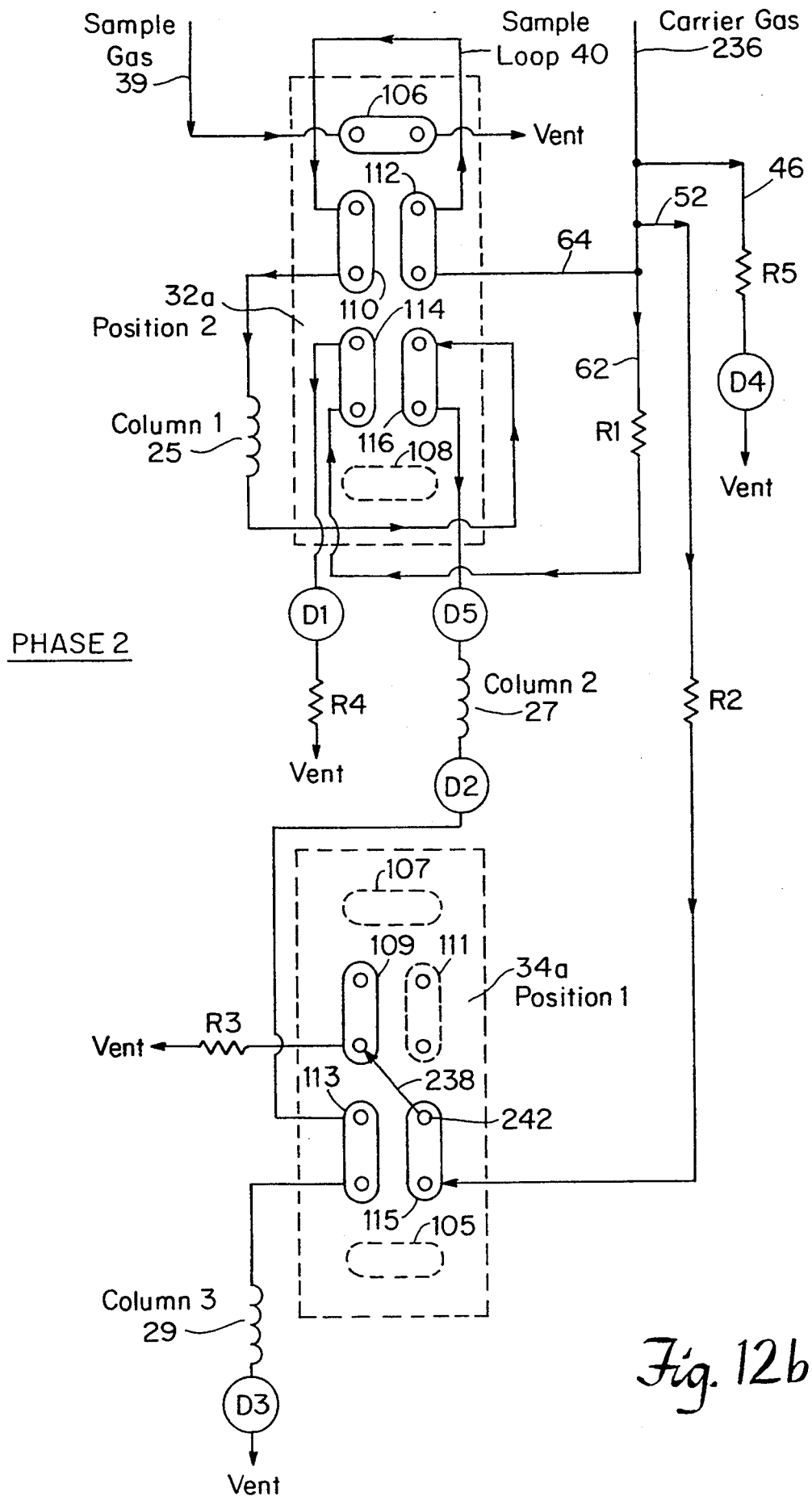
Figure 12C:
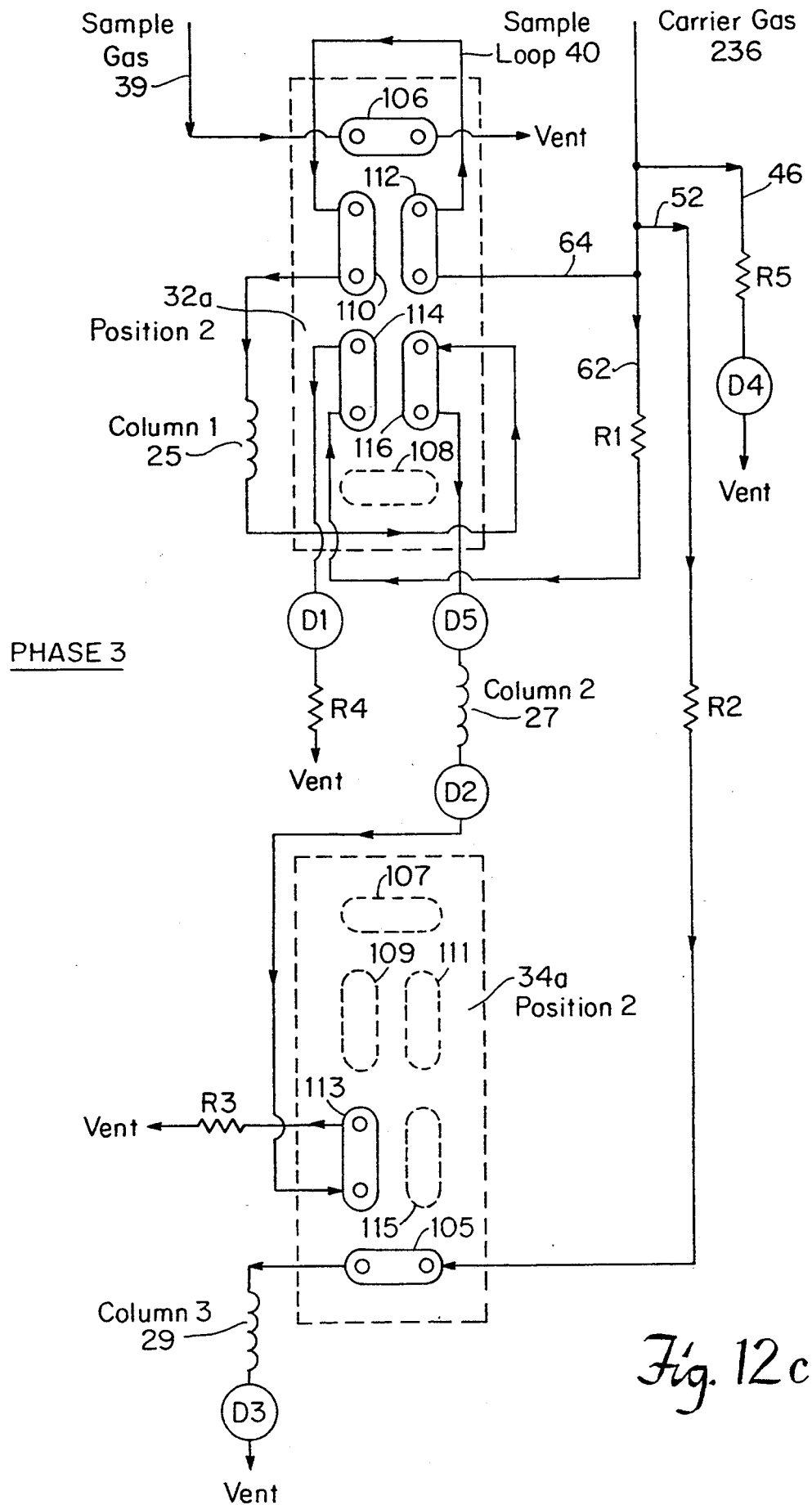

With reference to FIGS. 12a, 12b and 12c, the basic operation of the gas chromatography cartridge 10 is as follows. Sample gas from a source line 39 is directed to and accumulated in a sample loop 40. The use of a sample loop 40 as opposed to a gas port provides a precise volume of sample gas without turbulence and contamination by ambient air. The sample gas is subsequently inserted as a plug into a stream of the carrier gas such as helium by sliding valve face 32a from position 1 shown in FIG. 12a to position 2 shown in FIG. 12b. The combination of valve face positions will be discussed in greater detail below. The plug of sample gas and the carrier gas then pass through the three separation columns 25, 27 and 29. Three columns 25, 27 and 29 are provided rather than a single column because it often is necessary to pass the sample gas through multiple columns containing different stationary phases before its components are sufficiently separated for correct analysis. Detectors D1-D5 are appropriately positioned with respect to the separation columns 25, 27 and 29 to gather data regarding the content of gas that passes over the detectors D1-D5. Detector D5 detects components of sample gas after they exit the first column 25. Similarly, detectors D2 and D3 are positioned to detect the output of the second column 27 and the third column 29, respectively. Detector D1, in contrast, is used to detect gas when the first column 25 is back-flushed. Lastly, detector D4 can be used to provide an electrical reference signal because it only receives carrier gas during the tenure of the system's operation.

The flow through the columns 25, 27 and 29 and detectors D1-D5 is dictated by the position of the two sliders 32a and 34a housed in the slider valve assemblies 32 and 34, respectively. Restrictors R1-R5 are placed in the appropriate flow paths to maintain proper system flow. The sliders are positioned so that the gas passes through three consecutive columns as illustrated in FIGS. 12a. The pill shaped cavities in that figure represent the cavities in the slider face, and circles positioned in the pill-shaped cavities represent the gas ports of the manifold 26. Specifically, the circles positioned in the pill-shaped cavities of slider face 32a represent the gas ports 176 (FIGS. 6a, 6b and 6c), and the circles in the cavities of slider face 34a represent the gas ports 178 (FIGS. 6a, 6b and 6c). These ports will be mentioned again when discussing the manifold 26.

In the first phase shown in FIG. 12a, the sample gas is directed from the source line 39 through the sample loop 40 to the vent in order to fill the sample loop 40. The face of slider 32a, outlined in phantom form, is positioned in its first position so that the loop may be filled via cavities 110 and 112. Slider 34a is also in its first position. The unused cavities of both of the sliders 32a and 34a are shown in phantom form. The carrier gas from inlet 236, however, does not follow such a simple path; rather it branches out to several paths to flush the system. In particular, part of the carrier gas goes through branch 46 wherein it passes through restrictor R5 and the reference detector D4. After passing through the reference detector D4, the carrier gas is vented.

Part of the carrier gas also passes down branch 52. In branch 52 the carrier gas passes through a restrictor R2 and to cavity 115. Through the upper port 242 and a line 238 in the manifold 26, cavity 115 is coupled to cavity 109. The carrier gas flows through cavity 109 to another restrictor R3 and out a vent.

A final portion of the carrier gas is divided between branches 62 and 64. Gas in branch 62 passes through restrictor R1 and onto cavity 108. Having passed through cavity 108, the carrier gas passes through a detector D5, and subsequently through the second column 27 and detector D2, positioned after the column 27. Gas flowing past the detector D2 flows into cavity 113 which enables the carrier gas to flow to the third column 29 and later to detector D3, positioned after column 29. Lastly, the gas is vented.

The gas in branch 64 passes through cavity 116 and goes backwards through the first column 25 so as to back-flush the column. Once it has back-flushed column 25, the carrier gas passes through cavity 114 and detector D1. From detector D1, the carrier gas passes through the fourth restrictor R4 and is vented.

By positioning the sliders in their first positions as described above and shown in FIG. 12a for the first phase, the chromatography cartridge 10 achieves two objectives: first, it fills the sample loop so that a slug of sample gas can be injected, and second, it flushes contaminates from the columns 25, 27 and 29. As a result, the cartridge 10 is ready to receive the sample gas and perform chromatographical analysis on a new plug of sample gas.

In the second phase of operation illustrated in FIG. 12b, the chromatography cartridge 10 injects the sampled gas previously held in the sample loop 40 into the flow of the carrier gas. The sample gas no longer passes into the sample loop; rather the first slider 32a is adjusted to a second position to direct the flow through cavity 106. This cavity 106 bypasses the sample loop 40 and allows the sample gas to be directly vented. The carrier gas, in contrast, follows a flow similar to that of phase one. For instance, the carrier gas still flows down branches 46 and 52 in the same manner. However, the phases differ concerning branch 64. In particular, the slider 32a is adjusted to place cavity 112 in a position that causes the carrier gas to flow into the sample loop 40. As such, the plug of sample gas that was previously accumulated in the loop 40 in the first phase is injected into the flow of carrier gas. The carrier gas flows through the sample loop 40 and out through cavity 110. Cavity 110 directs the sample gas and carrier gas through the first column 25.

Once the sample gases have passed through the first column 25, they are somewhat separated into primary components. The gases are both directed to cavity 116 which guides them in the direction of detector D5. Once they have passed through detector D5, the gases pass through the second column 27 which further separates the sample gas components. Detector D2 is positioned after the second column 27. The sample gas/carrier gas combination continues to connection 113 which directs the gases to flow to the third column 29 for futher separation of the sample gas. A final detector D3 is positioned after the third column 29 for gathering additional data regarding the sample gas. Once the gases have passed through the third detector D3 they are vented.

The path 62 is significantly less complex than the path of branch 64. The carrier gas simply passes through the first restrictor R1 and into cavity 114. Subsequently, it flows through the first detector D1 and passes through a fourth restrictor R4 before being vented.

In the third phase of operation (FIG. 12c). Slider 32a remains in its second position while slider 34a is moved to a second position so that the sample gas only flows through two separation columns. Specifically, the carrier gas passes through branch 46 as described with respect to the previous phases. The flow of gas through branch 52 however, differs. Instead of flowing through cavity 115, the gas flows through cavity 105 into the third separation column 29. Once the gas has passed through the third separation column 29, it passes by detector D3 and is vented. Gas directed through branch 64 remains as it was in the second phase, except that the gas does not flow to the third column 29; rather it flows through cavity 113 to the third restrictor R3. From there, the gas is vented. The net effect of this arrangement is that branches 52 and 64 swap their respective trailing ends. Branch 62 flows as previously described for the second phase of operation.

The third phase of operation as depicted in FIG. 12c can be used in a number of ways, depending on the application. Its primary aim is to partition sample components. Some components are allowed to enter the third column in the second phase and others are vented in the third phase after passing through the second column and detector D2. Thus, as shown in FIG. 6c, in the third phase only pure carrier gas passes through the third column 29 to allow for the continued separation of the components that have already entered the third column 29 in the second phase. In these applications, the timing between phase 2 and phase 3 must be adjusted to make certain that only the desired components reach the third column in phase 2.

Figure 13:
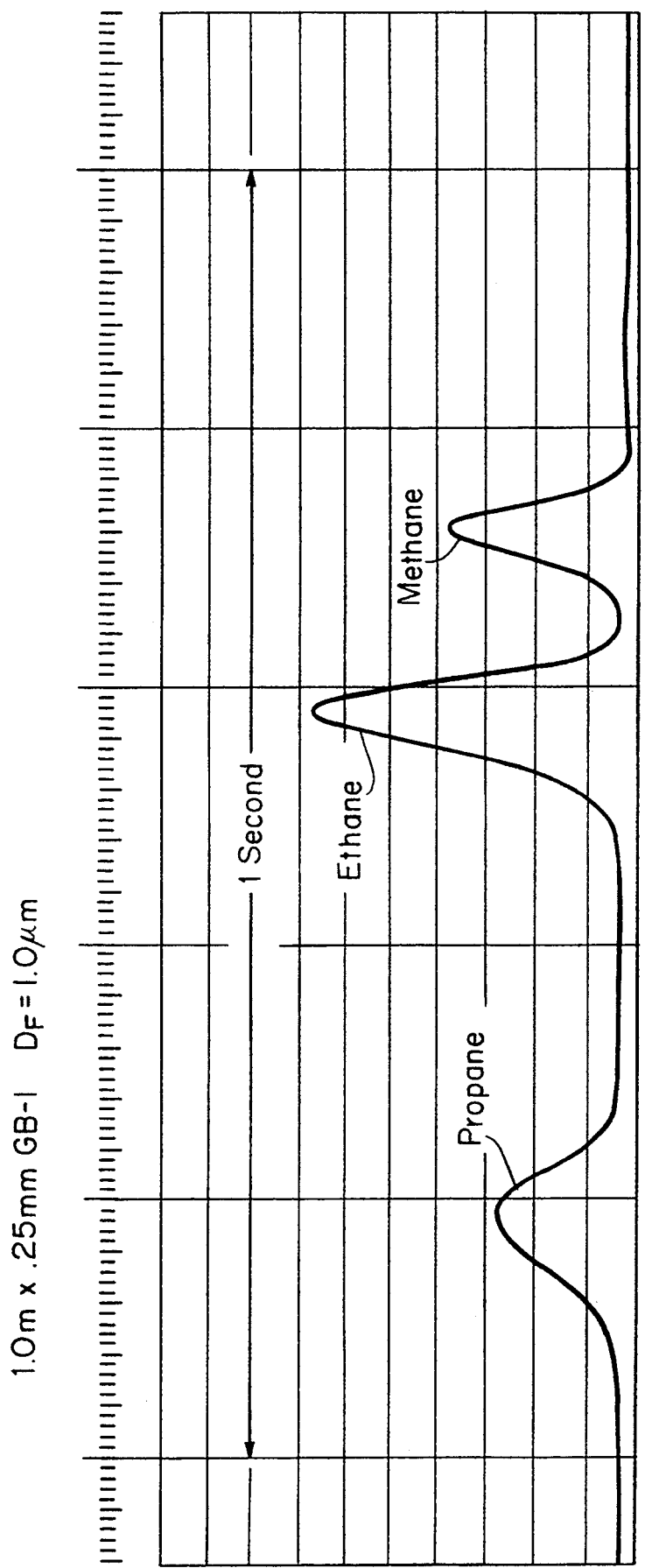
FIG. 13 depicts sample results obtained by the detectors.

The signals produced in response to plugs of sample components/carrier gas for a detector are exemplified in the results shown in FIG. 13 for a plug of sample gas comprised of propane, ethane and methane and carrier gas. Each of the sample gas components that flows past the detectors produces a set of such signals at a unique time measured from the time of injection that identifies each respective component. The chromatography cartridge 10 extracts the data produced by the detectors via the electrical connector 30 (FIG. 4). This data is processed by an adjacant data processing system (not shown) to provide the concentrations of the components from peak heights and areas of plotted curves of the data. FIG. 13 shows an ideal case where there is very distinct separation between the peaks. In practice, such separation is often not attainable, especially if only a single column is used. In many instances the peaks overlap. Thus, by using multiple columns containing different stationary phases greater separation of the peaks can be achieved. The magnitude and location of the peaks helps to identify and quantify the primary components of the sample gas.

The present invention provides several benefits over chromatography systems existing in the prior art. First, it is modular; hence, repair work can be done easily by replacing a non-working cartridge with a working cartridge. The non-working cartridge can then be carried back to a place of repair where repairs are effected more efficiently and more easily. Because of small size and ease of service, the chromatograph unit may be located in an otherwise inconvenient location closer to the sampling point. As a result, a reduction in cycle time is achieved by greatly reducing the sample transport time. A time savings is also realized by employing a small bore, thin film capillary columns rather than ⅛ inch packed columns used in the prior art. Chromatograph analysis times are, thus, reduced from minutes to seconds. Furthermore, much less sample is required than in previous systems, and the carrier gas flow rates are on the order of 1 ml/min as opposed to 60 ml/min which results in lower user costs. There is also the benefit of lower production costs due to the small size since fewer materials are necessary than in conventional systems. A final benefit is that the chromatography cartridge and chromatography system are designed to be safe so that the potential ill effects of an accident are minimized.

While the invention has been particularly shown and described with reference to a preferred embodiment thereof, it will be understood by those skilled in the art the various changes in form and detail may be made without departing from the spirit and scope of the inventions defined in the appended claims. For instance, the number of separation columns used may vary. Similarly, the type of separation columns may vary.

We claim:

1. A chromatography device for separating a sample fluid component from a sample fluid mixture carried by a carrier fluid and for analyzing the sample fluid component, comprising:
   a first housing portion having an internal space in which all electronic components of the device capable of igniting a flammable gas are housed;
   a second housing portion external to the first housing portion and having an interior space sealed relative to the interior space of the first housing portion, the second housing portion comprising:
   a) a column for separating the sample fluid component from the fluid mixture;
   b) a detector for detecting distinguishing characteristics of fluids exiting the column; and
   c) a manifold upon which the column and the detector are configured so as to form a replaceable modular chromatography cartridge, said manifold having a means for interconnecting a column of fluid sources and for attaching the cartridge to a support structure.

2. A chromatography device as recited in claim 1 wherein the column comprises a column with a stationary liquid phase on inner walls of the column.

3. A chromatography device as recited in claim 1 wherein the detector is a thermal conductivity detector.

4. A chromatography device as recited in claim 3 wherein a filament of the detector has a thickness in a range of magnitude of $10^{-6}$ meters.

5. A chromatography device as recited in claim 3 wherein a filament of the detector is comprised of platinum.

6. A chromatography device as recited in claim 5 wherein the detector includes a well under the filament so that fluids exiting the column surround the filament as they flow past the detector.

7. A chromatography device as recited in claim 1 wherein the manifold is initially comprised of a first plate and a second plate that are fused together and said means for interconnecting includes channels defined between said first and second plates.

8. A chromatography device as recited in claim 1 wherein the manifold is ceramic.

9. A chromatography device as recited in claim 1 wherein the second housing portion comprises an oven housing which surrounds the chromatography cartridge.

10. A chromatography device as recited in claim 9 further comprising an electrical heater located in the oven housing for providing heat in the oven housing to regulate the oven housing temperature.

11. A chromatography device as recited in claim 1 wherein connections between the first housing portion and the second housing portion consist essentially of detachable mechanical and electrical connections which allow the first housing portion and the second housing portion to be separated into two distinct portions and the cartridge to be replaced as a unit.

12. A chromatography device as recited in claim 1 wherein the first housing portion and the second housing portion are separable into two distinct portions without discontinuing electrical power to the chromatography device.

13. A chromatography device for separating a sample fluid component from a sample fluid mixture carried by a carrier fluid and for analyzing the sample fluid component, comprising:
 a first housing portion having an internal space in which all electronic components of the device capable of igniting a flammable gas are housed;
 a second housing portion external to the first housing portion and having an interior space sealed relative to the interior space of the first housing portion, the second housing portion comprising:
  a) a column for separating the sample fluid component from the fluid mixture;
  b) a detector for detecting distinguishing characteristics of fluid components exiting the column;
  c) a valve assembly for directing flow of the sample fluid and the carrier fluid through the device; and
  d) a manifold upon which the column, the detector and the valve assembly are configured to form a modular chromatography cartridge that may be replaced as a unit and through which all fluid connections for the cartridge are realized, said manifold having a means for attaching the cartridge to fluid sources and a support structure.

14. A chromatography device as recited in claim 13 wherein the detector is a thermal conductivity detector.

15. A chromatography device as recited in claim 13 wherein the valve assembly comprises at least one slider valve assembly driven by a solenoid in the first housing portion.

16. A chromatography device as recited in claim 15 wherein each slider valve assembly comprises a slider for directing fluid through the cartridge and a slider housing for housing the slider.

17. A chromatography device as recited in claim 16 wherein a spring assembly biases the slide assembly against an actuator from the solenoid.

18. A chromatography device as recited in claim 16 wherein the slider comprises a durable material smoothly slidable against the slider housing.

19. A chromatography device as recited in claim 13 wherein the second housing portion comprises an oven housing which surrounds the chromatography cartridge.

20. A chromatography device as recited in claim 10 further comprising an electrical heater located in the oven housing for providing heat in the oven housing to regulate the oven housing temperature.

21. A chromatography device as recited in claim 13 wherein connections between the first housing portion and the second housing portion consist essentially of detachable mechanical and electrical connections which allow the first housing portion and the second housing portion to be separated into two distinct portions and the cartridge to be replaced as a unit.

22. A chromatography device as recited in claim 13 wherein the first housing portion and the second housing portion are separable into two distinct portions without disconnecting electrical power to the chromatography device and the cartridge is replaceable as a unit.

23. A chromatography device for separating sample fluid components from a sample fluid mixture carried by a carrier fluid and for analyzing components of the sample fluid, comprising:
 a first housing portion having an internal space in which all electronic components of the device capable of igniting a flammable gas are housed;
 a second housing portion external to the first housing portion and having an interior space sealed relative to the interior space of the first housing portion, the second housing portion comprising:
  a) a plurality of columns for separating the sample fluid components from the fluid mixture;
  b) a plurality of detectors for detecting distinguishing characteristics of fluids exiting the columns;
  c) a valve assembly for directing flow of the sample fluid and the carrier fluid through the device to reconfigure flow of sample fluid through the columns;
  d) restrictors to balance the fluid flow rate of the carrier fluid when the valve assembly directs the fluid to not flow through a column as flow is reconfigured by the valve assembly; and
  e) a manifold upon which the columns, the detectors, the valve assembly and the restrictors are configured to form a modular gas chromatography cartridge that may be replaced as a unit and through which all fluid connections are realized, said manifold having a means for attaching the cartridge to fluid sources and a support structure.

24. A modular chromatography device as recited in claim 23 wherein the detectors are miniature detectors.

25. A modular chromatography device as recited in claim 23 wherein the valve assembly is comprised of a slider assembly for directing flow of the sample gas and the carrier gas through the cartridge driven by a solenoid in the first housing portion.

26. A modular chromatography device as recited in claim 23 wherein the restrictors comprise a flowpath threaded about a cylinder such that the amount of restriction of flow rate a restrictor produces is adjustable by varying the length of the flowpath threaded about the cylinder.

27. A modular chromatography device as recited in claim 26 wherein each restrictor includes a plastic sheath disposed between restrictor mating elements to reduce the formation of gaps between the mating elements as a result of expansion or contraction with temperature.

28. A modular chromatography device as recited in claim 27 wherein each plastic sheath surrounds a cylindrical major body portion of a restrictor in a concentric manner.

29. A chromatography device for processing a sample fluid mixture carried by a carrier fluid comprising:
 a first housing portion containing a solenoid and the electronics of the device carrying sufficient electrical energy to ignite flammable gases, and having an internal environment which is isolated from the environment of the remainder of the device;
 a second housing portion having an internal space accessible while maintaining isolation of the first housing portion and containing a column for separating a sample component from the sample fluid mixture, a detector for detecting distinguishing characteristics of fluids exiting the column, and a valve for controlling the flow of fluids to the column and the detector, the column, detector and valve being mounted together as a cartridge replaceable while maintaining isolation of the first housing portion, connections between the first portion and the second portion consisting essentially of a detachable mechanical coupling between the solenoid and the valve and a detachable electronic coupling between electronics of the first portion and electronics of the second portion.

30. A chromatography device as recited in claim 29 connected to a sampled process, wherein the cartridge comprises a fluid coupling for coupling all fluids between the cartridge and the process such that all fluid couplings between the process and cartridge are made simultaneously with replacement of the cartridge.

31. A chromatography device as recited in claim 30 wherein the cartridge is replaceable without disconnecting electrical power to the chromatography device.

32. A chromatography device as recited in claim 29 wherein the second portion contains a plurality of columns and a plurality of valves, and one mechanical connection between the first portion and the second portion exists for each valve located in the second portion.

33. A chromatography device as recited in claim 29 wherein the coupling between the solenoid and the valve is such that the solenoid pushes against a slide valve with no restricting linkage therebetween.

* * * * *